United States Patent
Sato et al.

(10) Patent No.: US 10,317,336 B2
(45) Date of Patent: Jun. 11, 2019

(54) SPECTRAL MEASUREMENT METHOD

(71) Applicant: OLYMPUS CORPORATION, Tokyo (JP)

(72) Inventors: Akira Sato, Tokyo (JP); Shinichi Takimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 214 days.

(21) Appl. No.: 15/227,086

(22) Filed: Aug. 3, 2016

(65) Prior Publication Data

US 2016/0341657 A1    Nov. 24, 2016

Related U.S. Application Data

(63) Continuation of application No. PCT/JP2014/054386, filed on Feb. 24, 2014.

(51) Int. Cl.
*G01J 3/28* (2006.01)
*G01N 21/27* (2006.01)
(Continued)

(52) U.S. Cl.
CPC ........... *G01N 21/27* (2013.01); *G01J 3/00* (2013.01); *G01J 3/28* (2013.01); *G01J 3/44* (2013.01);
(Continued)

(58) Field of Classification Search
CPC .......... G01J 3/28; G01J 3/00; G01J 2003/283; G01N 21/27; G01N 21/65
(Continued)

(56) References Cited

U.S. PATENT DOCUMENTS

| | | | |
|---|---|---|---|
| 2007/0104394 A1* | 5/2007 | Chou | G06T 3/4007 382/300 |
| 2009/0310132 A1* | 12/2009 | Bennett | G01J 3/02 356/301 |

(Continued)

FOREIGN PATENT DOCUMENTS

| JP | 201025622 A | 2/2010 |
|---|---|---|
| JP | 2010517029 A | 5/2010 |

(Continued)

OTHER PUBLICATIONS

International Search Report dated Mar. 18, 2014, issued in PCT/JP2014/054386.

(Continued)

*Primary Examiner* — John E Breene
*Assistant Examiner* — Jeffrey P Aiello
(74) *Attorney, Agent, or Firm* — Scully, Scott, Murphy & Presser, P.C.

(57) ABSTRACT

A spectral measurement method of the present invention includes: a measuring step of measuring optical spectra of some sections specified among a plurality of sections on a specimen; a scalar-value calculating step of calculating, for individual measured sections, scalar values that represent information contained in the obtained optical spectra; an interpolating step of interpolating scalar values of unmeasured sections by using the calculated scalar values and by using two types of interpolation methods; an identifying step of identifying sections in which absolute values of differences between the two scalar values interpolated by using the two types of interpolation methods are equal to or greater than a predetermined threshold; and a repeating step of re-executing steps from the measuring step to the identifying step after specifying the identified sections.

13 Claims, 5 Drawing Sheets

(51) Int. Cl.
*G01N 21/65* (2006.01)
*G01J 3/00* (2006.01)
*G01J 3/44* (2006.01)

(52) U.S. Cl.
CPC ........ *G01N 21/65* (2013.01); *G01J 2003/283* (2013.01); *G01N 2201/12* (2013.01)

(58) Field of Classification Search
USPC .................................. 356/73, 326; 702/189
See application file for complete search history.

(56) References Cited

U.S. PATENT DOCUMENTS

| | | | |
|---|---|---|---|
| 2011/0267340 A1 | 11/2011 | Kraus et al. | |
| 2013/0222408 A1* | 8/2013 | Lee | G09G 3/3466 345/589 |
| 2013/0278578 A1* | 10/2013 | Vetsuypens | G09G 3/20 345/207 |
| 2014/0347452 A1* | 11/2014 | Smolic | H04N 13/0011 348/54 |
| 2015/0131090 A1* | 5/2015 | Osumi | G01J 3/504 356/300 |
| 2015/0171890 A1* | 6/2015 | Pagnanelli | H03M 3/468 341/143 |
| 2015/0369664 A1* | 12/2015 | Garsha | G01J 3/10 356/402 |

FOREIGN PATENT DOCUMENTS

| | | |
|---|---|---|
| JP | 2013525035 A | 6/2013 |
| JP | 2014038043 A | 2/2014 |
| WO | WO2008090350 A1 | 7/2008 |
| WO | WO2011139895 A1 | 11/2011 |

OTHER PUBLICATIONS

Drumm, C. et al. "Microscopic Raman Line-Imaging with Principal Component Analysis", 1995 vol. 49, No. 9 pp. 1331-1337.

* cited by examiner

SPECTRAL MEASUREMENT METHOD

CROSS-REFERENCE TO RELATED APPLICATIONS

This is a continuation of International Application PCT/JP2014/054386 which is hereby incorporated by reference herein in its entirety.

TECHNICAL FIELD

The present invention relates to a spectral measurement method.

BACKGROUND ART

In the related art, in order to acquire information about components contained in a specimen, specific types of light coming from individual positions of the specimen are detected, optical spectra, such as Raman spectra, infrared absorption spectra, or the like, are acquired by diffracting the detected light, and the acquired optical spectra are analyzed (for example, see Patent Literature 1 and Non-Patent Literature 1).

In the case in which the light coming from the specimen is weak, it takes time to measure the optical spectrum once, and thus, it takes longer to acquire sufficient numbers of optical spectra. In Patent Literature 1 and Non-Patent Literature 1, the overall measurement time is reduced by simultaneously acquiring optical spectra at a plurality of positions by using line-shaped illumination light or by synchronizing the charge read-out of a detector that detects light coming from the specimen and scanning of the illumination light.

CITATION LIST

Patent Literature

{PTL 1} Japanese Translation of PCT International Application, Publication No. 2010-517029

Non-Patent Literature

{NPL 1} Charlene A., Drumm, and one other, "Microscopic Raman Line-Imaging with Principal Component Analysis", Applied Spectroscopy, Vol. 49, Issue 9, pp. 1331-1337 (1995)

SUMMARY OF INVENTION

Solution to Problem

The present invention provides a spectral measurement method including: a measuring step of measuring optical spectra of some sections specified among a plurality of sections constituting a measurement region on a specimen; a scalar-value calculating step of calculating, for the individual sections measured in the measuring step, scalar values that represent information contained in the optical spectra by analyzing the optical spectra acquired in the measuring step; an interpolating step of interpolating scalar values of sections that have not been measured in the measuring step by using the scalar values calculated in the scalar-value calculating step and by using two types of interpolation methods; an identifying step of identifying sections in which absolute values of differences between the two scalar values interpolated in the interpolating step by using the two types of interpolation methods are equal to or greater than a predetermined threshold; and a repeating step of re-executing the measuring step, the scalar-value calculating step, the interpolating step, and the identifying step after specifying the sections identified in the identifying step.

DESCRIPTION OF EMBODIMENT

A spectral measurement method according to an embodiment of the present invention will be described below with reference to the drawings.

Figure 1:
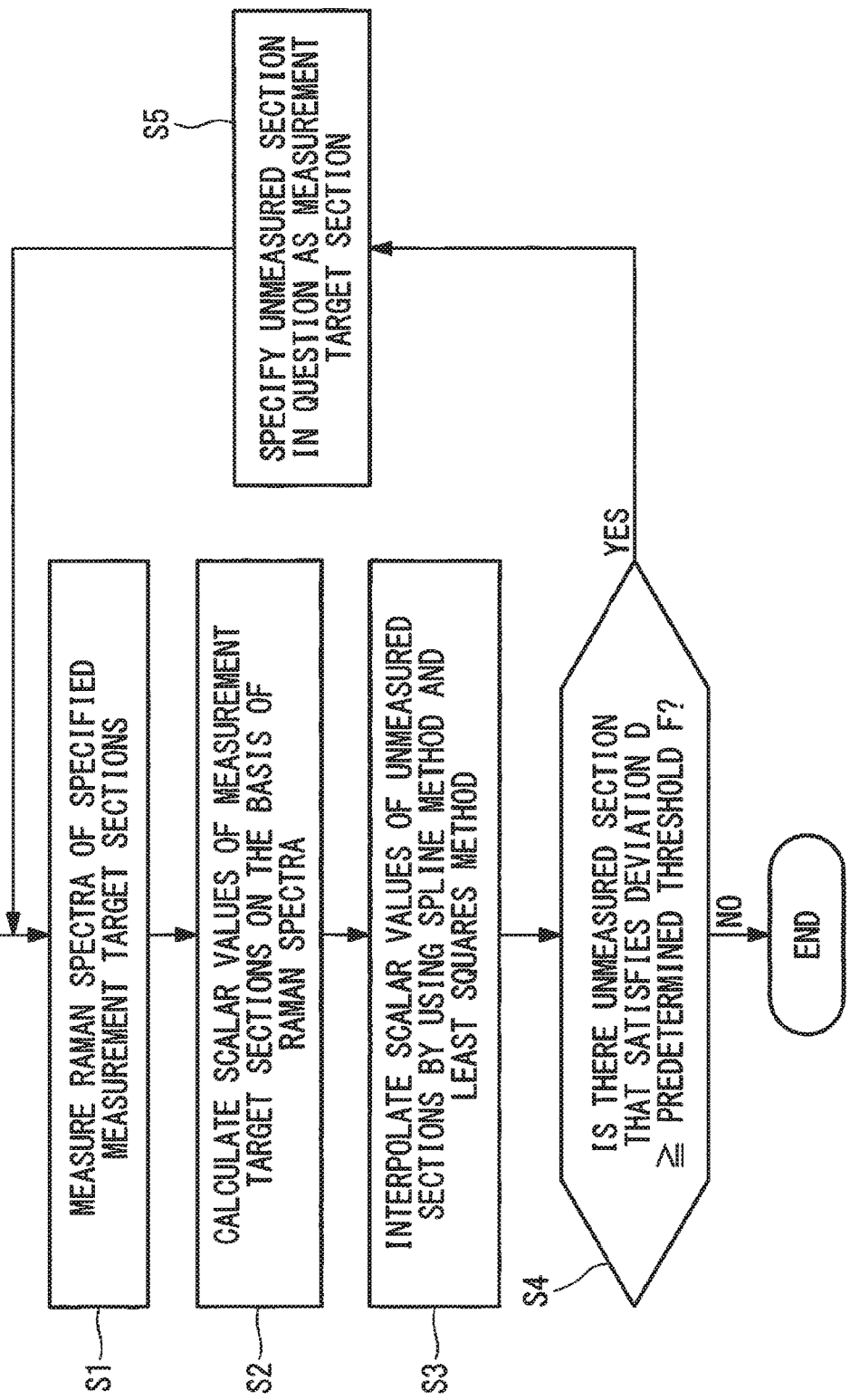
FIG. 1 is a flowchart showing a spectral measurement method according to an embodiment of the present invention.

As shown in FIG. 1, the spectral measurement method according to this embodiment includes: a measuring step S1 of measuring optical spectra of a specimen at some sections in an observation region by using a microscope; a scalar-value calculating step S2 of calculating scalar values on the basis of the optical spectra acquired in the measuring step S1; an interpolating step S3 of interpolating scalar values of sections that were not measured in the measuring step S1 by using two types of interpolation methods; an identifying step S4 of identifying unmeasured sections in which deviations D between the two scalar values interpolated in the interpolating step S3 are greater than a predetermined threshold F; and a repeating step S5 of repeating the procedures from the measuring step S1 to the identifying step S4 after specifying the sections identified in the identifying step S4.

Such a spectral measurement method is employed in a microscope system provided with a microscope that acquires optical spectra that contain information about molecules contained in a specimen by detecting light coming from the specimen by irradiating the specimen with illumination light and a control device that analyzes the optical spectra acquired by the microscope and that controls the microscope on the basis of the analysis results. For example, the control device is a computer provided with a CPU (Central Processing Unit) and a storage device, and the spectral measurement method of this embodiment is stored in the storage device in the form of a program. Then, the CPU reads out the program from the storage device and executes the program, thus performing the processing from the measuring step S1 to the repeating step S5, described above. Alternatively, the control device may be provided with a scalar-value calculating portion, an interpolating portion, an identifying portion, and a repeating portion so as to serve as special hardware for executing the individual processing in steps S2, S3, S4, and S5 among the steps S1 to S5.

Figure 2:
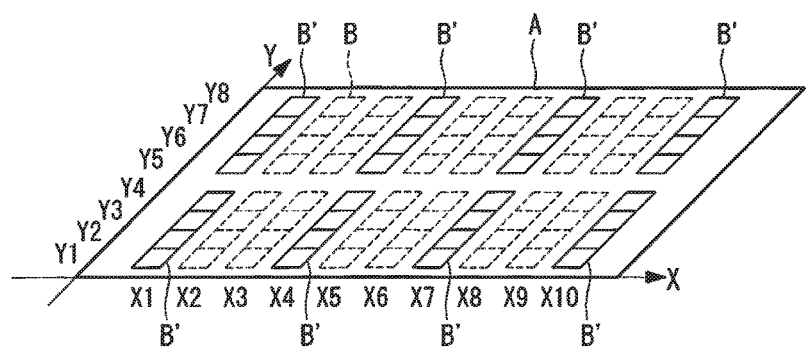
FIG. 2 is a diagram for explaining sections that form an observation region of a specimen to be measured by using the spectral measurement method in FIG. 1.

First, in the measuring step S1, optical spectra of some sections among a plurality of sections constituting an observation region are measured by using the microscope. As shown in FIG. 2, an observation region A on the specimen is sectioned into a plurality of sections B that are arranged in two axial directions (X-direction and Y-direction). The control device specifies some sections among these sections B as measurement target sections B' and the optical spectra are measured only for the specified measurement target sections B' by using the microscope. In this embodiment, a total of 80 sections B are set, ten arranged in the X-axis direction and eight each in the Y-axis direction, and, of these 80 sections B, 32 sections B corresponding to X=X1, X4, X7, and X10 are specified as the measurement target sections B'.

Figure 3:
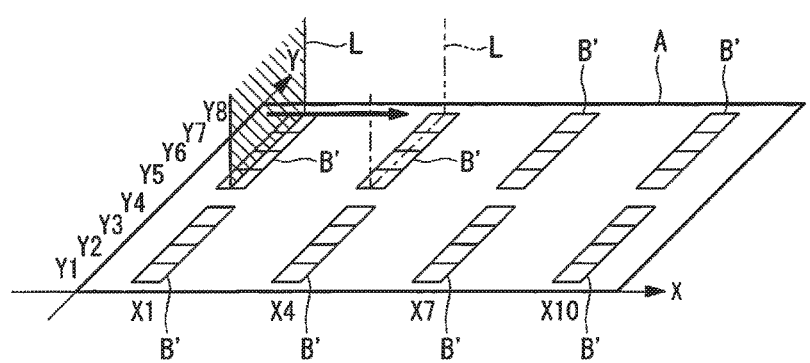
FIG. 3 is a diagram for explaining a measuring step of the spectral measurement method in FIG. 1.

As shown in FIG. 3, the microscope irradiates, on the basis of instructions from the control device, the measurement target sections B' with line-shaped illumination light L that extends in the X-axis direction, detects light generated at the measurement target sections B', and acquires optical spectra of the individual measurement target sections B' by diffracting the detected light. Thus, the microscope acquires optical spectra of all of the specified measurement target sections B' by repeating the optical-spectrum acquisition after moving, in the X-axis direction and the Y-axis direction, the positions to be irradiated with the illumination light L. At this time, the microscope simultaneously acquires optical spectra of a plurality of measurement target sections B' by simultaneously radiating the line-shaped illumination light L onto the plurality of (four in the illustrated example) measurement target sections B' that are arranged in the Y-axis direction.

Note that, it is possible to change, as appropriate, the method with which Raman spectra are measured by using the microscope. For example, spot-shaped illumination light may be used instead of the line-shaped illumination light L. In this case, a Raman spectrum of one measurement target section B' is acquired by performing the measurement once.

As the optical spectra to be measured by using the microscope in this embodiment, Raman spectra will be described below. Other than Raman spectra, the optical spectra measured by using the spectral measurement method of this embodiment may be near-infrared absorption spectra, mid-infrared absorption spectra, far-infrared absorption spectra, visible absorption spectra, ultraviolet absorption spectra, or fluorescence spectra.

Next, in the scalar-value calculating step S2, information contained in the Raman spectra at the individual measurement target sections B', for example, scalar values representing intensities or the like of Raman scattered light coming from specific molecules are calculated by analyzing the Raman spectra acquired in the measuring step S1. For example, principal component loadings are calculated by performing principal component analysis on a hyper Raman spectrum, which is a collection of all acquired Raman spectra, principal component scores, which are inner products of the principal component loadings and the individual Raman spectra, are calculated, and the principal component scores are used as the scalar values of the measurement target sections B' at which the Raman spectra have been measured.

Alternatively, an independent component analysis may be performed on the hyper Raman spectrum, and the inner products of the acquired independent component vectors and the individual Raman spectra may be used as the scalar values of the measurement target sections B' at which the Raman spectra have been measured, or band intensities (peak intensities or area intensities) of the individual Raman spectra in a predetermined frequency band may be used as the scalar values of the measurement target sections B'.

Alternatively, after performing a cluster analysis, such as singular value decomposition, NNMF (Non Negative Matrix Factorization), or the like, on the hyper Raman spectrum, inner products of component vectors representing the classified individual clusters and the optical spectra may be used as the scalar values of the measurement target sections B'. Furthermore, inner products of endmember vectors, which are calculated by performing a VCA (Vertex Component Analysis) on the hyper Raman spectrum, and the optical spectra may be used as the scalar values of the measurement target sections B'.

Figure 4:
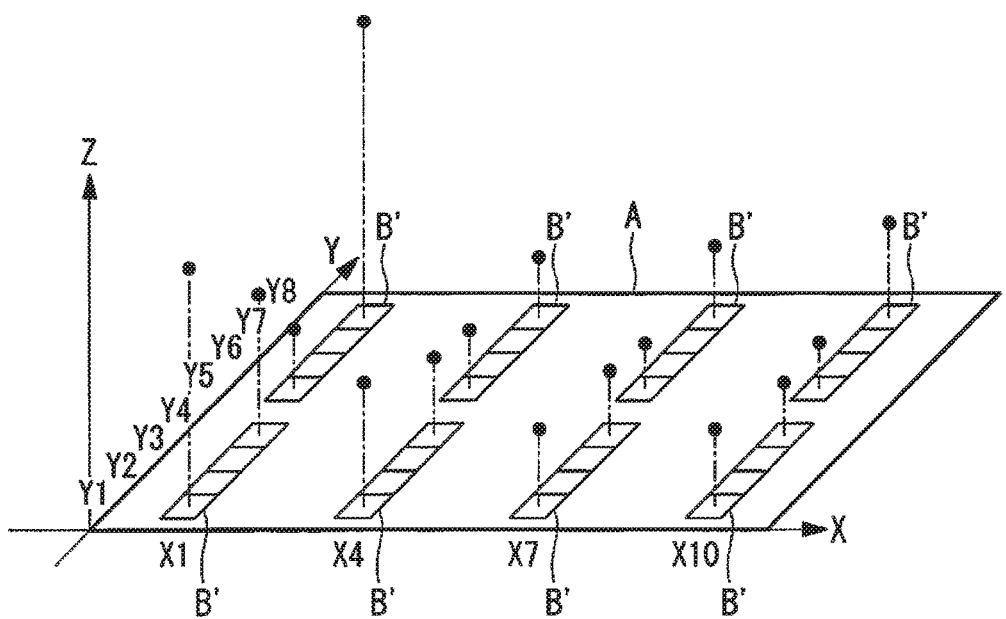
FIG. 4 is a diagram for explaining an interpolating step of the spectral measurement method in FIG. 1, showing an X-Y-Z space when an observation surface is set on the X-Y-axes and scalar values are set on the Z-axis.

Next, in the interpolating step S3, scalar values of unmeasured sections B are interpolated by using the scalar values of the individual measurement target sections B' calculated in the scalar-value calculating step S2. Specifically, two types of interpolation methods are used to obtain two types of approximation curves that approximate changes of scalar values Z of the measurement target sections B' in the X-axis direction. In FIG. 4, the individual scalar values Z (see filled dots) are plotted in X-Z-planes in which the positions of the measurement target sections B' in the X-axis direction are set on the horizontal axis (X-axis) and the scalar values Z are set on the vertical axis (Z-axis). FIG. 4 shows an X-Y-Z space in order to simultaneously illustrate a plurality of X-Z-planes arranged in the Y-axis direction. In addition, FIG. 4 shows the scalar values Z only for some of the measurement target sections B' in order to prevent the figure from becoming complicated.

In this embodiment, a spline method and a least squares method, which are interpolation methods employing a polynomial expression, will be described as the two types of interpolation methods. With the spline method, a spline curve is calculated based on a polynomial expression such that the curve passes through individual plotted points and smoothly connects the points. With the least squares method, a least squares curve is calculated based on a polynomial expression such that the sum of squares of errors with respect to the scalar values arranged in the X-axis direction is minimized.

Figure 5A:
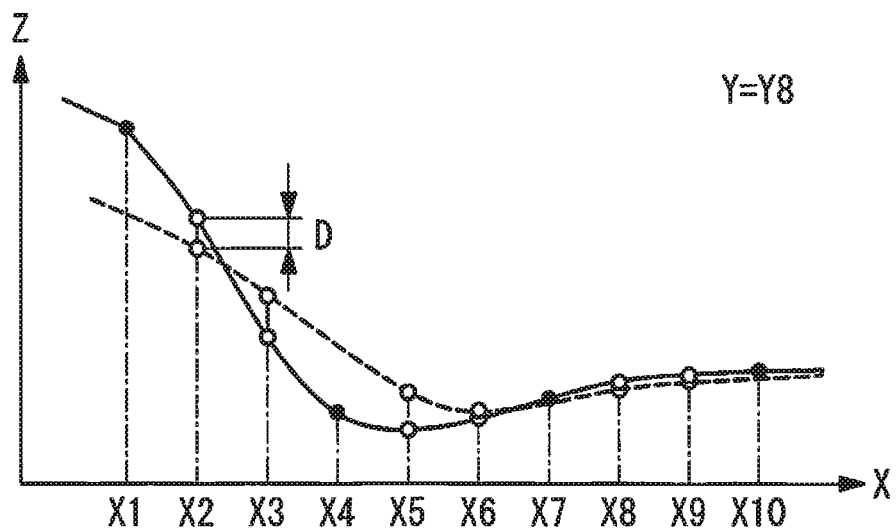
FIG. 5A is a diagram showing an X-Z-plane when Y=Y8 in FIG. 4 and is a diagram for explaining processing for interpolating the scalar values of unmeasured sections by using a spline curve (solid line) and a least squares curve (broken line).
Figure 5B:
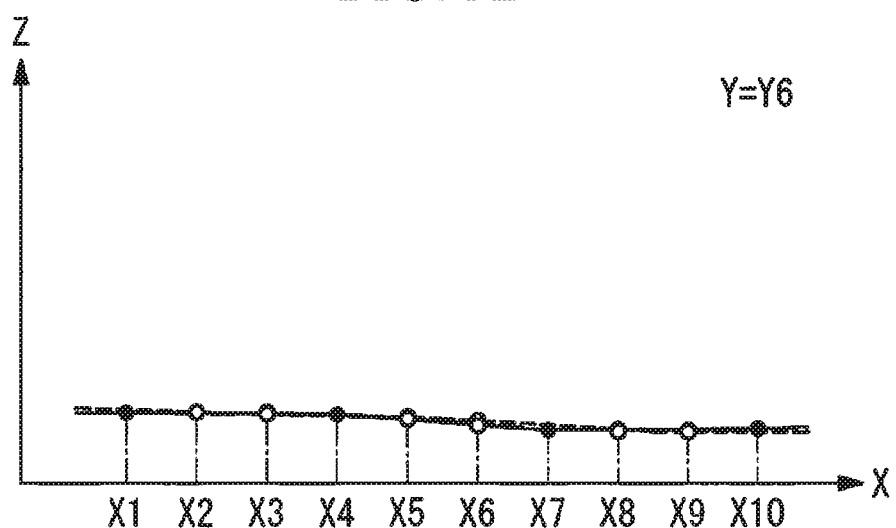
FIG. 5B is a diagram showing an X-Z-plane when Y=Y6 in FIG. 4 and is a diagram for explaining processing for interpolating the scalar values of unmeasured sections by using a spline curve (solid line) and a least squares curve (broken line).

FIGS. 5A and 5B show the calculated spline curve (solid line) and least squares curve (broken line) drawn in the X-Z-planes. FIG. 5A shows an X-Z-plane at Y=Y8, where the scalar values Z exhibit relatively large changes in the X-axis direction, and FIG. 5B shows an X-Z-plane at Y=Y6, where the scalar values Z exhibit relatively small changes in the X-axis direction. The scalar values of the unmeasured sections B are interpolated by using the two approximation curves. As shown in FIGS. 5A and 5B, the scalar values of individual positions interpolated by using the two approximation curves having different properties greatly deviate from each other in a region in which the scalar values Z exhibit large changes, and become substantially equal to each other in a region in which the scalar values Z exhibit small changes.

Next, in the identifying step S4, unmeasured sections B in which scalar values need to be acquired are identified on the basis of deviations D, in the individual unmeasured sections B, between the two approximation curves calculated in the interpolating step S3. Specifically, the deviations D are calculated in the form of absolute values of differences between the scalar values Z based on the least squares method and the scalar values Z based on the spline method at X=X2, X3, X5, X6, X8, and X9 corresponding to the unmeasured sections B. Then, unmeasured sections B in which the obtained deviations D are greater than a predetermined threshold F are identified. The identification of the unmeasured sections B in which the deviations D are greater than the predetermined threshold F is executed for all X-Z-planes for Y=Y1 to Y8.

Next, in the repeating step S5, the unmeasured sections B identified in the identifying step S4 are newly specified as the measurement target sections B', and the Raman spectra of the newly-specified measurement target sections B' are acquired by using the microscope. By doing so, processing from the above-described measuring step S1 to identifying step S4 is repeated no more unmeasured sections B are identified in the identifying step S4.

Figure 6:
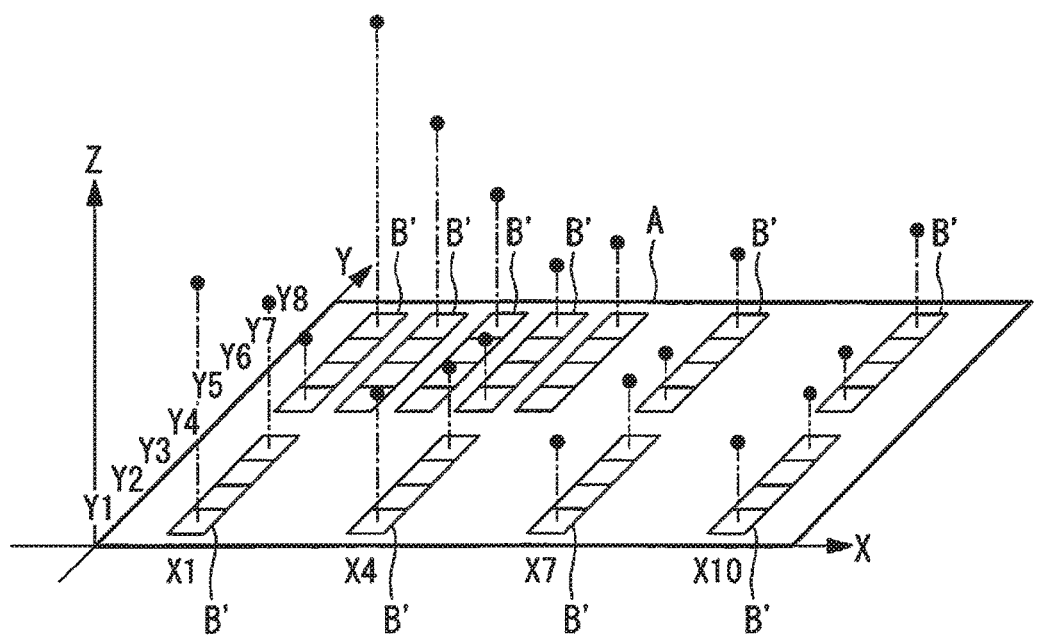
FIG. 6 shows an X-Y-Z space in which new scalar values are added in the second interpolating step.

For example, X=X2, X3, and X5 in FIG. 5A, where the deviations D are relatively large, are identified in the repeating step S5. In this case, the Raman spectra of sections B at X=X2, X3, and X5 and Y=Y8 are additionally acquired in the second measuring step S1, and, the scalar values are calculated from the newly-acquired Raman spectra in the second scalar-value calculating step S2. Then, in the second interpolating step S3, the newly-calculated scalar values Z are added to the X-Z-planes as shown in FIG. 6, changes in the scalar values at X=X1 to X6, X7, and X10, which include the previously-calculated scalar values and the newly-calculated scalar values are approximated by using the two types of approximation curves, and thus, the interpolation is performed for the scalar values of the unmeasured sections B in which all scalar values that have previously been calculated are taken into consideration.

As has been described, with this embodiment, first, the Raman spectra are measured by omitting some sections B from all sections B in the observation region A, and the scalar values of the sections B that have not been measured are estimated by using the two types of interpolation methods. Then, in the case in which the deviations D between the scalar values estimated by using the two types of interpolation methods are sufficiently large, that is, in the case in which there is a large change in characteristics, such as molecular contents, in the measurement subject in those unmeasured sections B, and thus, the Raman spectra of the unmeasured sections B in question contain important information for an observer, the Raman spectra of those unmeasured sections B are additionally measured.

The amount of time required for measuring the Raman spectra once is greater as compared with the amount of time required for performing computational processing like steps S2, S3, and S4, and this amount of time required for measuring the Raman spectra is an obstacle to reducing the overall processing time. With this embodiment, the Raman spectra of the sections B containing important information for the observer are additionally measured in a reliable manner while reducing the number of times the Raman spectra are measured, and thus, there is an advantage in that it is possible to effectively reduce the overall measurement time while ensuring a sufficiently high spatial measurement precision.

Note that, in this embodiment, although the scalar values of the unmeasured sections B are two-dimensionally interpolated in the interpolating step S3 by using the two types of interpolation methods, alternatively, three-dimensional interpolation may be employed. In this case, two types of interpolation methods are used to obtain three-dimensional approximation curved planes that approximate changes at the individual points in the X-Y-directions plotted in an X-Y-Z space like the one shown in FIG. 4. As the two types of interpolation methods, for example, the spline method and an inverse-distance-weighting method or a Kriging method are used.

In the case in which the scalar values of the unmeasured sections B are two-dimensionally interpolated in the X-axis direction, as in FIGS. 5A and 5B, changes of the scalar values of the measurement target sections B' in the Y-axis direction are not taken into consideration when interpolating the scalar values of the unmeasured sections B. As opposed to this, because changes in the measured scalar values in the two-dimensional directions are taken into consideration in the case of three-dimensional interpolation, it is possible to interpolate the scalar values of the unmeasured sections B with greater precision.

With this modification, for example, the following processing is performed in the identifying step S4. The deviations D are calculated in the form of the absolute values of the differences between the scalar values Z of the two types of approximation curved planes calculated in the interpolating step S3, and regions in which the calculated deviations D are greater than the predetermined threshold F are identified. Then, the positions of the center of gravity in the X-Y-planes are calculated for the identified regions. In the repeating step S5, regions including the positions of the center of gravity calculated in the identifying step S4 are specified as the new measurement target sections. In this way, by using the regions including the positions of the center of gravity as additional measurement target sections, it is possible to minimize the number of times the Raman spectra are additionally measured.

Alternatively, the center positions of the unmeasured sections B may be set in advance as sample points, and the deviations D at the sample points may be compared with the predetermined threshold F. In addition, regions in which the deviations D are greater than the predetermined threshold F may be identified, the identified regions may be divided into a plurality of sections, and the divided individual sections may be specified as new measurement target sections.

In addition, in this embodiment, although the Raman spectra are measured in the measuring step S1 by using the sections B that are regularly arrayed in the observation region A as the measurement unit, alternatively, the Raman spectra may be measured by specifying the measurement target sections in an irregular manner.

The above-described embodiment leads to the following inventions.

The present invention provides a spectral measurement method including: a measuring step of measuring optical spectra of some sections specified among a plurality of sections constituting a measurement region on a specimen; a scalar-value calculating step of calculating, for the individual sections measured in the measuring step, scalar values that represent information contained in the optical spectra by analyzing the optical spectra acquired in the measuring step; an interpolating step of interpolating scalar values of sections that have not been measured in the measuring step by using the scalar values calculated in the scalar-value calculating step and by using two types of interpolation methods; an identifying step of identifying sections in which absolute values of differences between the two scalar values interpolated in the interpolating step by using the two types of interpolation methods are equal to or greater than a predetermined threshold; and a repeating step of re-executing the measuring step, the scalar-value calculating step, the interpolating step, and the identifying step after specifying the sections identified in the identifying step.

With the present invention, on the basis of the optical spectra of some sections in the observation region measured in the measuring step, information about components contained in the specimen in those sections can be acquired in the form of the scalar values in the scalar-value calculating step.

In this case, the scalar values of the sections that have not been measured in the measuring step are interpolated in the interpolating step by using the two types of interpolation methods.

The two scalar values interpolated by using different types of interpolation methods become substantially equal to each other in a region in which the calculated scalar values exhibit sufficiently small changes, and differ from each other in a region in which the calculated scalar values exhibit sufficiently large changes. A region in which the scalar values exhibit large changes is a region in which the characteristics of components in the specimen targeted for measurement greatly change, and thus, it is an important region for the observer. Sections qualifying as part of such an important region are identified in the identifying step, optical spectra thereof are additionally measured in the repeating step, and thus, the scalar values thereof are additionally calculated.

In this way, with some sections omitted, the optical spectra are measured in the first measuring step, and the optical spectra are additionally measured for sections that contain important information for the observer and that have not been measured. By doing so, it is possible to reduce the overall measurement time while maintaining a sufficiently high spatial measurement precision.

In the above-described invention, by irradiating a plurality of the sections that are arranged in a single row with line-shaped illumination light and by detecting light coming from the plurality of sections, the optical spectra of the plurality of the sections may simultaneously be measured in the measuring step.

By doing so, it is possible to further reduce the overall measurement time.

In the above-described invention, the optical spectra of a plurality of the sections that are arranged in a single row may be measured in the measuring step and, in the interpolating step, by using the scalar values of the plurality of the sections that are arranged in the single row, scalar values of the sections that are included in the same row as the plurality of the sections and that have not been measured may be interpolated in the arraying direction of the plurality of the sections.

By doing so, the scalar values of the unmeasured sections are interpolated by using a row as a unit, and thus, the invention is suitable for the case in which the sections are arrayed in a regular manner.

In the above-described invention, the two types of interpolation methods may be a spline interpolation method and a least squares method.

By doing so, it is possible to more reliably identify sections that are important for the observer by making the deviations of the scalar values interpolated by using the two types of interpolation methods sufficiently large in a region in which the scalar values exhibit large changes.

In the above-described invention, the optical spectra of a plurality of the sections distributed in two-dimensional directions may be measured in the measuring step, and, in the interpolating step, by using the scalar values of the plurality of the sections distributed in the two-dimensional directions, scalar values of the sections that have not been measured may be interpolated in the two-dimensional directions.

By doing so, it is possible to more accurately interpolate the scalar values of the unmeasured sections by taking into consideration the changes in the scalar values in the two-dimensional directions.

In the above-described invention, the two types of interpolation methods may be two methods among a spline interpolation method, an inverse-distance-weighting interpolation method, and a Kriging interpolation method.

By doing so, it is possible to more reliably identify sections that are important for the observer by making the deviations of the scalar values interpolated by using the two types of interpolation methods sufficiently large in a region in which the scalar values exhibit large changes.

In the above-described invention, the scalar values may be inner products of the optical spectra and principal component loadings obtained by performing principal component analysis on a collection of the optical spectra of the plurality of the sections; the scalar values may be inner products of the optical spectra and independent component vectors obtained by performing independent component analysis on a collection of the optical spectra of the plurality of the sections; or the scalar values may be intensities of the optical spectra in predetermined frequency bands or intensity ratios of two predetermined frequency bands. Alternatively, the scalar values may be inner products of the optical spectra and component vectors classified by means of a cluster analysis, such as singular value decomposition, NNMF (Non Negative Matrix Factorization), or the like, or the scalar values may be inner products of the optical spectra and endmember vectors separated by means of a VCA (Vertex Component Analysis).

By doing so, it is possible to analyze the distribution of specific components contained in the specimen.

In the above-described invention, the optical spectra may be Raman spectra, near-infrared absorption spectra, mid-infrared absorption spectra, far-infrared absorption spectra, visible absorption spectra, ultraviolet absorption spectra, or fluorescence spectra.

By doing so, it is possible to analyze the distribution of specific components contained in the specimen.

REFERENCE SIGNS LIST

L illumination light
A observation region
B section
B' measurement target section
S1 measuring step
S2 scalar-value calculating step
S3 interpolating step
S4 identifying step
S5 repeating step

The invention claimed is:
1. A spectral measurement method comprising:
a measuring step of measuring optical spectra of specified individual sections specified among a plurality of sections constituting a measurement region on a specimen;

a scalar-value calculating step of calculating, for the specified individual sections measured in the measuring step, scalar values that represent information contained in the optical spectra by analyzing the optical spectra acquired in the measuring step;

an interpolating step of interpolating scalar values of sections that have not been measured in the measuring step by using the scalar values calculated in the scalar-value calculating step and by using two types of interpolation methods;

an identifying step of identifying sections in which absolute values of differences between the two scalar values interpolated in the interpolating step by using the two types of interpolation methods are equal to or greater than a predetermined threshold; and re-executing the measuring step, the scalar-value calculating step, the interpolating step, and the identifying step, wherein the measuring step is re-executed to measure optical spectra of the sections identified in the identifying step as the specified individual sections specified among the plurality of sections constituting the measurement region on the specimen.

2. The spectral measurement method according to claim 1,
wherein the measuring step comprises:
irradiating a plurality of the specified individual sections that are arranged in a single row with line-shaped illumination light; and
detecting light coming from the plurality of the specified individual sections, to simultaneously measure the optical spectra of the plurality of the specified individual sections.

3. The spectral measurement method according to claim 1,
wherein the measuring step comprises measuring the optical spectra of the specified individual sections that are arranged in a single row, and
wherein the interpolating step comprises interpolating scalar values of the sections that are included in the same row as the specified individual sections and that have not been measured by using the scalar values calculated in the scalar-value calculating step and by using the two types of interpolation methods.

4. The spectral measurement method according to claim 3,
wherein the two types of interpolation methods are a spline interpolation method and a least squares method.

5. The spectral measurement method according to claim 1,
wherein the plurality of sections are distributed in two-dimensional directions.

6. The spectral measurement method according to claim 5,
wherein the two types of interpolation methods are two methods among a spline interpolation method, an inverse-distance-weighting interpolation method, and a Kriging interpolation method.

7. The spectral measurement method according to claim 1,
wherein the scalar values are inner products of the optical spectra and principal component loadings obtained by performing principal component analysis on a collection of the optical spectra of the plurality of the sections.

8. The spectral measurement method according to claim 1,
wherein the scalar values are inner products of the optical spectra and independent component vectors obtained by performing independent component analysis on a collection of the optical spectra of the plurality of the sections.

9. The spectral measurement method according to claim 1,
wherein the scalar values are intensities of the optical spectra in predetermined frequency bands or intensity ratios of two predetermined frequency bands.

10. The spectral measurement method according to claim 1,
wherein the scalar values are inner products of the optical spectra and vectors corresponding to spectra that represent individual clusters acquired by means of a cluster analysis based on singular value decomposition or NNMF (Non Negative Matrix Factorization).

11. The spectral measurement method according to claim 1,
wherein the optical spectra are Raman spectra, near-infrared absorption spectra, mid-infrared absorption spectra, far-infrared absorption spectra, visible absorption spectra, ultraviolet absorption spectra, or fluorescence spectra.

12. A system comprising:
a processor comprising hardware, wherein the processor is configured to at least perform:
a measuring step of controlling a microscope to measure optical spectra of specified individual sections specified among a plurality of sections constituting a measurement region on a specimen;
a scalar-value calculating step of calculating, for the specified individual sections measured in the measuring step, scalar values that represent information contained in the optical spectra by analyzing the optical spectra acquired in the measuring step;
an interpolating step of interpolating scalar values of sections that have not been measured in the measuring step by using the scalar values calculated in the scalar-value calculating step and by using two types of interpolation methods;
an identifying step of identifying sections in which absolute values of differences between the two scalar values interpolated in the interpolating step by using the two types of interpolation methods are equal to or greater than a predetermined threshold; and
re-executing the measuring step, the scalar-value calculating step, the interpolating step, and the identifying step, wherein the measuring step is re-executed to measure optical spectra of the sections identified in the identifying step as the specified individual sections specified among the plurality of sections constituting the measurement region on the specimen.

13. A computer-readable non-transitory storage medium storing instructions that cause a computer to at least perform:
a measuring step of controlling a microscope to measure optical spectra of specified individual sections specified among a plurality of sections constituting a measurement region on a specimen;
a scalar-value calculating step of calculating, for the specified individual sections measured in the measuring step, scalar values that represent information contained in the optical spectra by analyzing the optical spectra acquired in the measuring step;

an interpolating step of interpolating scalar values of sections that have not been measured in the measuring step by using the scalar values calculated in the scalar-value calculating step and by using two types of interpolation methods;

an identifying step of identifying sections in which absolute values of differences between the two scalar values interpolated in the interpolating step by using the two types of interpolation methods are equal to or greater than a predetermined threshold; and re-executing the measuring step, the scalar-value calculating step, the interpolating step, and the identifying step, wherein the measuring step is re-executed to measure optical spectra of the sections identified in the identifying step as the specified individual sections specified among the plurality of sections constituting the measurement region on the specimen.

* * * * *